United States Patent [19]
Wilson

[11] Patent Number: 5,305,753
[45] Date of Patent: Apr. 26, 1994

[54] METHOD AND APPARATUS FOR DETERMINING THE VELOCITY OF A FLOWING LIQUID

[75] Inventor: Laurence S. Wilson, Allambie Heights, Australia

[73] Assignee: Commonwealth Scientific and Industrial Research Organisation, Campbell, Australia

[21] Appl. No.: 941,088
[22] PCT Filed: Apr. 18, 1991
[86] PCT No.: PCT/AU91/00143
§ 371 Date: Oct. 29, 1992
§ 102(e) Date: Oct. 29, 1992
[87] PCT Pub. No.: WO91/16000
PCT Pub. Date: Oct. 31, 1991

[30] Foreign Application Priority Data
Apr. 18, 1990 [AU] Australia .................. PJ9658

[51] Int. Cl.$^5$ ................................ A61B 8/00
[52] U.S. Cl. ................................ 128/661.08
[58] Field of Search ............ 128/660.05, 661.08, 128/661.09, 661.10; 73/861.25

[56] References Cited
U.S. PATENT DOCUMENTS 5,050,611  9/1991  Takamizawa et al. ......... 128/661.09
5,105,817  4/1992  Uchibori et al. ............. 128/661.08
5,190,044  3/1993  Kawasaki et al. ............. 128/661.09

Primary Examiner—William E. Kamm
Assistant Examiner—George Manuel
Attorney, Agent, or Firm—Ladas & Parry

[57] ABSTRACT

Calculation of the two-dimensional velocity vector of liquid flowing through a region which is imaged in a B-mode ultrasonic echoscopy display involves dividing the region into a number of small, preferably rectangular, cells. One of the cells is scanned rapidly, at least twice, by a beam of ultrasonic energy which is transmitted sequentially along a number of lines of sight which intersect the cell. An image of the cell is formed from the signals reflected from scatterers within the liquid in the cell during each scan of the cell. The two-dimensional brightness functions, $S(x,y)$, of each image of the cell form a data set $S(x,y,t)$ after the repeated scanning. The data set $S(x,y,t)$ is integrated separately with respect to x and y by projection onto the $(x,t)$ and $(y,t)$ planes. Using the projected functions of $S(x,y,t)$, the average velocity of the scatterers in the cell (and hence of the liquid flowing through the cell) is obtained in the x-direction and in the y-direction. From these two average velocities, the magnitude and direction of the two-dimensional velocity vector is obtained, and displayed on the echogram. The scanning, imaging and computational procedures are then repeated for another of the cells.

10 Claims, 3 Drawing Sheets

METHOD AND APPARATUS FOR DETERMINING THE VELOCITY OF A FLOWING LIQUID

TECHNICAL FIELD

This invention relates to the measurement of liquid flow. It provides a method and apparatus for the determination of both the direction and magnitude of the two-dimensional velocity of small samples of a flowing liquid. It is particularly, but not exclusively, useful in the investigation of blood flow through vessels or parts of vessels in the human body, for which purpose ultrasonic echoscopy has been used previously. Thus the present invention is an alternative to the conventional measurement of liquid flow using the Doppler frequency shift of ultrasonic signals which have been reflected by ultrasound scatterers in suspension in a flowing liquid.

BACKGROUND OF THE INVENTION

It is now well known that ultrasonic echoscopy techniques can be used to provide information about an object that is not visible to the eye. The basic technique of ultrasonic echoscopy involves directing a short pulse of ultrasonic energy, typically in the frequency range from 1 MHz to 30 MHz, into the region of the object that is being examined, and observing the energy that is reflected, as an echo, from each acoustic impedance discontinuity in that region. Each echo received is converted into an electrical signal and displayed as either a blip or an intensified spot on a single trace of a cathode ray tube or television screen. Such a display of the echoes is known as an "A-mode" echograph or echogram, and is useful in a number of diagnostic techniques to locate the boundaries of the object or to provide other information about the region into which the pulse of ultrasonic energy has been directed.

If a series of adjacent A-mode displays are obtained (for example, by physically or electrically moving the transmitting transducer which produces the pulses of ultrasonic energy, or by scanning the direction of transmission of the pulses of ultrasonic energy), a two-dimensional image of the object under examination may be displayed on the cathode ray tube or television screen. Such an image or display of acoustic discontinuities, which corresponds to the structure of the object, is known as a "B-mode" image or display.

The use of the Doppler frequency shift in the ultrasonic examination of flowing liquids and moving objects is also well known. Many echoscopes which perform the B-mode imaging examination described above can also perform Doppler frequency shift measurements in respect of echoes returned from moving objects within the region receiving ultrasonic energy from the echoscope. When the object under examination is a blood vessel, measurement of the Doppler shift of echoes from the blood cells within the vessel permits the velocity of those blood cells to be estimated. As pointed out by R W Gill, in his article entitled "Measurement of Blood Flow by Ultrasound: Accuracy and Sources of Error", which was published in *Ultrasound in Medicine and Biology*, Volume 11 (1985), pages 625 to 641, it is possible to measure the total volume of flow per unit time using an ultrasonic examination technique which includes the measurement of frequency changes due to the Doppler effect.

In ultrasonic examinations including Doppler frequency shift measurements, it is necessary to obtain echoes from a limited volume of the flowing liquid which is within the vessel being examined. This is achieved by fixing the line of sight of the ultrasonic transducer and, in the most commonly used version of Doppler measurement known as "pulsed Doppler", analyzing the echoes obtained from the sample volume for a limited range of time delays. The Doppler shift in the received echoes is averaged in order to calculate the average speed of scatterers in the flowing liquid.

In current implementations of the pulsed Doppler technique, the quantity measured as "velocity" is actually the component of velocity measured along the line of sight of a beam of ultrasound. Therefore the actual velocity (magnitude and direction) of the flowing liquid is not determined, although it can sometimes be inferred (for example, when the flow is along a vessel with clearly-imaged walls, as in the case of blood flow through an artery).

The information obtained by applying the Doppler technique to ultrasound measurements is commonly displayed in one of two ways or modes.

The first mode, known as a spectral display, is used when ultrasound pulses are repeatedly transmitted down the same line of sight, and echoes from a small region (the "sample volume") are selected for analysis. This selection is effected by accepting only echoes received within a certain range of delay times after transmission of the ultrasound pulses. The frequency spectrum observed, over a series of transmitted pulses, as a result of mixing the returned echoes with the transmitted frequency, corresponds to the spectrum of velocities in the flowing liquid that is being examined. This spectrum is displayed in a two-dimensional form with a horizontal axis representing time and a vertical axis representing velocity, and with the brightness of the displayed data corresponding to the strength of Doppler signal (which is approximately proportional to the number of scatterers in the flowing liquid at that time moving with the indicated velocity). Information about the direction and distribution of flow velocities, as well as their time evolution, may be inferred from this kind of display. The physical principles involved in this form of velocity display are well explained by K J W Taylor, P N Burns and P N T Wells in their book entitled "Clinical Applications of Doppler Ultrasound", published by Raven Press (1988).

The other commonly employed display mode is usually termed "color Doppler imaging". This display mode incorporates Doppler frequency shift information into a conventional ultrasound image. In this display mode, selected ultrasound lines of sight are repeated several times in rapid succession. Doppler shift measurements are taken for a number of sample volumes down each of the selected lines of sight. By suitable arrangement of the selected lines of sight, the whole or a part of the imaged area can be covered with a grid of sample volumes. A simplified version of the Doppler spectrum is calculated, and the liquid velocity is displayed by coloring the area of the ultrasound image which is covered by the sample volume. The color indicates the direction (towards or away from the transducer) and approximate magnitude of the velocity. In some applications of the color Doppler imaging technique, the spread of velocities can also be displayed. The display is updated in real time and gives an overview of liquid dynamics over an extended region. This technique has been described by K Miyatake, M Okamoto, N Kinoshita, S Izumi, M Owa, S Takao, H Sakakibara and Y Nimura in their article entitled "Clinical applications of a new type of real-time two-dimensional flow imaging system", which was published in *American Journal of Cardiology*, volume 54 (1984), pages 857–868.

In both the spectral and color Doppler imaging display techniques, the displayed velocity is actually the component along the line of sight, as indicated in the well-known Doppler equation:

$$f_D = \frac{2 f_0 v \cos\theta}{c} \quad (1)$$

in which $f_D$ is the Doppler frequency shift, $f_0$ is the ultrasound frequency, v is the velocity of the liquid, c is the speed of sound in the medium and $\theta$ is the angle between the flow vector and the ultrasonic line of sight. Thus changes in the Doppler frequency shift $f_D$ may be due to changes in the liquid velocity v, or they may be due to changes in the angle $\theta$. In some cases (for example, when there is undisturbed flow along a straight vessel), the angle $\theta$ may be inferred from the vessel orientation. A technique for doing this automatically is described by L S Wilson, M J Dadd and R W Gill in the specification of International patent application No PCT/AU91/00026. However, in many instances where liquid flow is being investigated by applying Doppler frequency shift measurements to ultrasound, the absolute magnitude and direction of the flow velocity cannot be easily inferred from the value of one velocity component.

Clearly it is desirable to be able to measure two orthogonal components of the velocity of a flowing liquid, to enable its velocity vector to be determined, and several alternative methods of doing this have been proposed. For example, M D Fox, in an article entitled "Multiple crossed beam ultrasound Doppler velocimetryle", published in *IEEE Transactions on Sonics and Ultrasonics*, volume SU-25 (1978), pages 281–286, describes the use of several transducers viewing the region of flow from different directions to obtain several velocity components. In addition, G E Trahey, S M Hubbard and O T von Ramm, in their article entitled "Angle independent ultrasonic blood flow detection by frame-to-frame correlation of B-mode images", published in *Ultrasonics*, volume 26 (1986), pages 271–276, describe the use of two-dimensional cross-correlation between successive B-mode image frames to determine the blood velocity vector. However, the first approach (described by Fox) uses a non-standard transducer arrangement, while the second approach (described by Trahey et al) requires larger computing power, making real time implementation of the technique difficult.

DISCLOSURE OF THE PRESENT INVENTION

It is an object of the present invention to provide a novel, effective method, and apparatus, for measuring the velocity of a flowing liquid in two orthogonal directions (the x-direction and the y-direction), and in a manner which enables the two-dimensional vector velocity to be displayed in real time.

This objective is achieved by dividing the region of interest in a B-mode image into a number of sub-images or small cells, and scanning one of the cells or sub-images several times in rapid succession with a beam of ultrasound. The signals reflected from the cell during each scan are subjected to conventional video processing to produce a two-dimensional brightness function, $S(x,y)$, which varies as each scan of the cell is performed. The brightness function is then integrated with respect to x and y, to obtain projected functions on the $(x,t)$ and $(y,t)$ planes. From these projected functions, the average velocities, in each cell, in the x-direction and in the y-direction, are obtained. Knowing these velocities, an average velocity vector for the x,y plane of the cell can be obtained and, if required, displayed. This scanning, video processing and signal analysis procedure is then repeated for another cell or sub-image of the region of interest.

Thus, according to the present invention, there is provided a method of determining the two-dimensional velocity vector of liquid flowing through a region which is included in a B-mode ultrasonic echoscopy display of at least a part of an object, said B-mode display being created from an analysis of the ultrasonic echoes received from a beam of ultrasonic energy which is scanned over said at least part of said object, said scanning being effected by the sequential transmission into said object of said beam of ultrasonic energy along a plurality of lines of sight, each line of sight being spatially displaced relative to its preceding, adjacent line of sight, said method comprising the steps of (a) selecting, from said B-mode display, a plurality of small cells within said region, each cell being intersected by a plurality of said lines of sight;

(b) for a selected one of said cells, scanning the ultrasonic beam at least twice in rapid succession over the lines of sight which pass through the cell and, for each scan, subjecting the signals reflected from scatterers within the cell to conventional video processing and producing a two dimensional brightness function $S(x,y)$, and subsequently creating a data set $S(x,y,t)$ of the image of the cell;

(c) for the selected cell, integrating the data set $S(x,y,t)$ separately with respect to x and y, by projecting $S(x,y,t)$ onto the $(x,t)$ and $(y,t)$ planes to obtain projected functions $S_x(x,t)$ and $S_y(y,t)$, respectively;

(d) for the selected cell, determining, from said projected functions $S_x(x,t)$ and $S_y(y,t)$, the average velocity of the scatterers within the cell, and hence of the liquid flowing through the cell, (i) in the x-direction ($<v_x>$) and (ii) in the y-direction ($<v_y>$);

(e) for the selected cell, determining, from the average velocity in the x-direction and the average velocity in the y-direction, the two-dimensional velocity vector of the liquid flowing through the cell; and (f) repeating steps (b), (c), (d) and (e) for another one of the cells.

Normally, the two-dimensional vector velocity of the liquid flowing through the cell will be displayed on the B-mode image.

Preferably, step (d) is effected by computing the two-dimensional Fourier transforms of the projected functions and performing a summation of the squared magnitudes of the two-dimensional Fourier transforms.

The cell shapes are preferably (but not necessarily) substantially rectangular. The cells or sub-images may comprise a linear array of cells (for example, when the region of interest is a line crossing a vessel), or they may cover a two-dimensional area, depending on the region of interest that is being investigated.

If required, and if the flow in the z-direction is zero, the liquid flow rate through a defined region can be determined from the vector sum of the two-dimensional vector velocities of the small cells which make up the region.

Also according to the present invention, there is provided apparatus for obtaining values of the two-dimensional velocity vector of liquid flowing through a region of a vessel, the apparatus comprising
- (a) an echoscope adapted to produce a B-mode echogram of at least part of the vessel which includes said region;
- (b) means for defining a plurality of small cells within the image of the region in the B-mode echogram;
- (c) means associated with the echoscope for scanning a selected one of said cells with a beam of ultrasonic energy by transmitting said beam of ultrasonic energy into said selected cell sequentially along a plurality of lines of sight which intersect said cell, for monitoring signals reflected from ultrasonic scatterers within said selected cell, and for forming a two-dimensional image from the reflected signals, defined by a brightness function $S(x,y)$;
- (d) programmed computation means adapted
  - (i) to receive a plurality of said brightness functions $S(x,y)$ obtained from sequential scanning of the selected cell with said beam of ultrasonic energy, and to store the resultant data set $S(x,y,t)$;
  - (ii) to integrate the data set $S(x,y,t)$ separately with respect to x and y by projecting $S(x,y,t)$ onto the (x,t) and (y,t) planes, and thereby obtain projected functions $S_x(x,t)$ and $S_y(y,t)$, respectively;
  - (iii) to determine, from said projected functions $S_x(x,t)$ and $S_y(y,t)$, the average velocity of the scatterers within the cell, and hence of the liquid flowing through the cell, in the x-direction ($<v_x>$) and in the Y-direction ($<v_y>$); and
  - (iv) to obtain, from the average velocity in the x-direction and the average velocity in the y-direction, the two-dimensional velocity vector of the liquid flowing through the cell; and
- (e) velocity display means associated with the echoscope to incorporate into said B-mode image a display of the magnitude, and possibly the direction, of the two-dimensional velocity vector of liquid flowing through the cell.

For a better understanding of the present invention, an embodiment of the invention will now be described (by way of example example only). In the following description, reference will be made to the accompanying drawings.

DETAILED DESCRIPTION OF THE ILLUSTRATED EMBODIMENT

Figure 1:
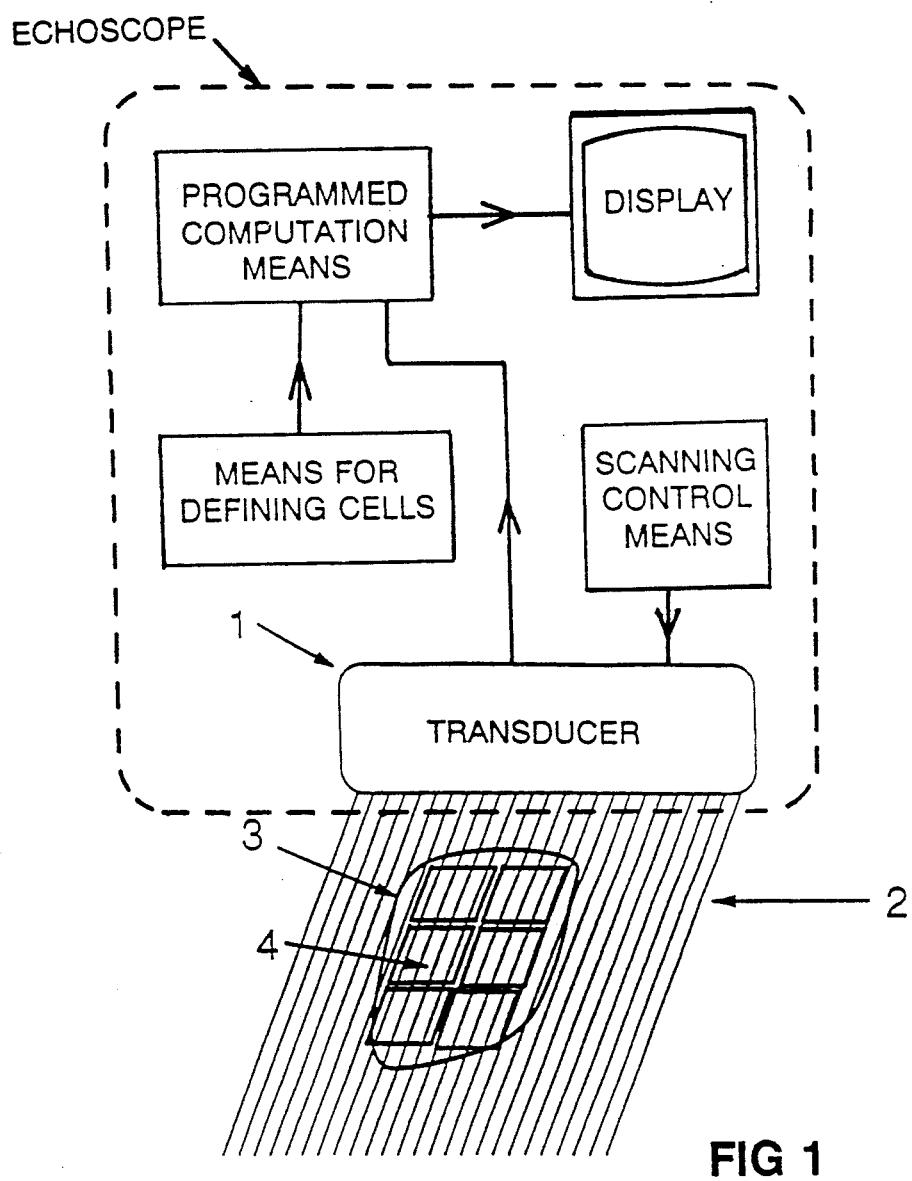
FIG. 1 is a schematic representation of an echoscope, showing features required for the present invention, the region of interest and the designation of cells within that region.

The present invention comprises a scan mode and a processing algorithm which can be applied to a suitable echoscope. FIG. 1 illustrates one implementation of apparatus used to perform the invention.

FIG. 1 shows an echoscope which produces the echogram display of a linear array transducer 1. The transducer 1 generates a beam of ultrasonic energy which is scanned across a region 3 of a B-mode display. A liquid is flowing through the region 3, which need not be a region constrained by walls which coincide with the periphery of the region. The scanning of the ultrasound beam is effected by transmitting the ultrasound beam sequentially along the lines of sight 2 which intersect the object which contains the region 3 that is of interest to the operator of the echoscope. Although FIG. 1 shows the use of a linear array transducer (the preferred transducer for implementation of the present invention), other types of transducer which can generate and scan a beam of ultrasound (for example, a phased sector scanning transducer) can be used in place of the linear array transducer 1.

Figure 5:
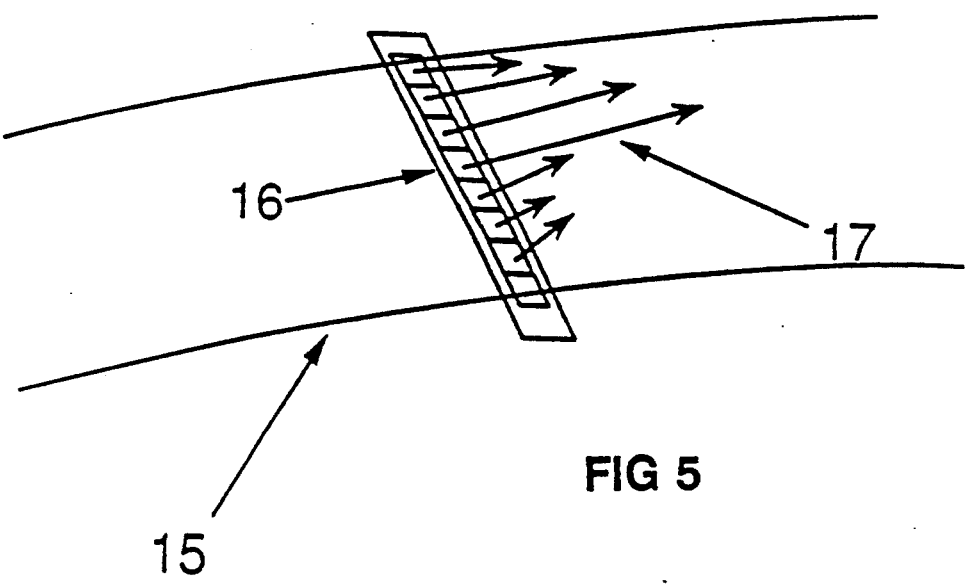
FIG. 5 shows one way in which velocities, obtained using the present invention, may be displayed.

The operator of the echoscope, having identified the region of interest 3, divides the image of the region into a number of small sub-images or cells 4. In FIG. 1, the cells 4 are shown as substantially square cells, but the cells may have other rectangular shapes, or be trapezoidal. The transverse dimensions of the cells are chosen so that each cell is intersected by a number of lines of sight 2. Usually four or eight lines of sight will intersect a cell, but the cell dimension can be chosen so that any suitable number of lines of sight intersect the cell. The axial dimension of a cell will normally be substantially the same as the transverse dimension. Cells may overlap. Since each cell undergoes separate processing when the method of the present invention is applied, the cells need not all be the same shape. The region of interest may be a straight line in a vessel, in which case the cells will form a linear array of sub-images within the B-mode display (as shown in FIG. 5).

One of the sub-images or cells 4 is then selected and the ultrasound beam is scanned rapidly at least twice, and preferably at least four times, over that cell. In the prototype equipment produced to test the present invention, the scanning of a cell is usually effected eight times. The time between scans should be as short as possible.

Although one cell is scanned a number of times while the remainder of the cells in the region of interest are ignored, other cells located along, and therefore sharing, the same lines of sight will, of course, be scanned at the same time.

The echoes from each scan of the cell are subjected to conventional video processing (that is, they pass through a demodulation, or envelope detection amplifier) and an image of cell is produced, for each scan, as a two-dimensional brightness function, $S(x,y)$. The combination of the images obtained from the sequence of scans thus produces a data set $S(x,y,t)$, where x is the spatial dimension perpendicular to the lines of sight, y is the spatial dimension parallel to the lines of sight and t is the time dimension (counting the number of scans of the cell).

The data set $S(x,y,t)$ is then integrated separately with respect to both x and y. This is effected by projecting $S(x,y,t)$ onto the (x,t) and (y,t) planes, respectively. The two projected functions are referred to as $S_x(x,t)$ and $S_y(y,t)$. The projections of each frame onto the two spatial axes are preferably done on a frame-by-frame basis.

Figure 2:
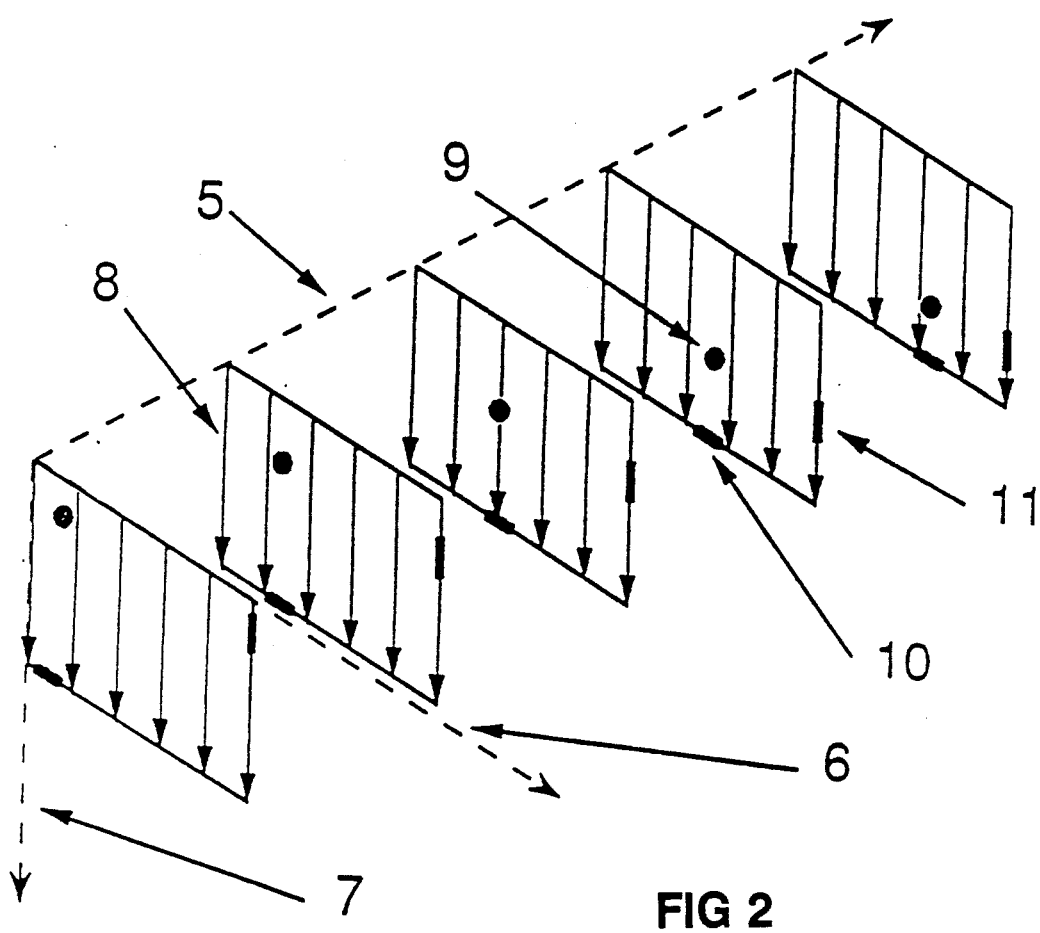
FIG. 2 illustrates the principles used in obtaining projection functions for a single cell.

FIG. 2 is a representation of the time evolution of one cell. The three axes shown are the time axis 5 (counting the number of scans of the cell), the x axis 6 (showing the lines of sight within a cell) and the depth axis 7 (corresponding to the time delay of the received echoes for a line of sight within the cell). The lines of sight within each cell are represented by vertical arrows 8. A scatterer 9 is shown moving across the cell, and its position may be plotted within each cell. Its projection 10 onto the x axis and its projection 11 onto the y axis are shown, and demonstrate the effects of the two components of its motion.

The two projected functions $S_x(x,t)$ and $S_y(y,t)$ are next analyzed to determine the average velocity components $<v_x>$ and $<v_y>$. This is preferably achieved by the following algorithm.

The two-dimensional Fourier transform of the two functions $S_x(x,t)$ and $S_y(y,t)$ is computed. This is preferably done after multiplying by suitable window functions, then increasing the size of the arrays by adding an array of zero elements. This practice results in increased precision in the resulting measurements. A suitable size (after adding the zero elements) is 32 elements by 32 elements. The squared magnitude of the two-dimensional Fourier transform is analyzed by the following method.

Each pixel in the two-dimensional Fourier transform corresponds to a small range of velocities in the original data. The relevant formula for the x velocity component is:

$$v(j, k) = \frac{\delta x}{\delta t} \cdot \frac{k}{j} \quad (2)$$

wherein (j,k) are the element numbers in the two-dimensional Fourier transform, x is the sampling interval in x and t is the time between frames (scans). Note that all pixels along a line with a given slope intersecting the origin of the two-dimensional frequency domain correspond to the same velocity. A similar formula applies to the y velocity component.

The average velocity in each of the two directions is found by performing a summation over the pixels in the two-dimensional Fourier domain, using the formulae:

$$<v_x> = \frac{\sum_{j,k} \frac{\delta x}{\delta t} \frac{k}{j} F_x(j, k)}{\sum_{j,k} F_x(j, k)}$$

and $$<v_y> = \frac{\sum_{j,k} \frac{\delta y}{\delta t} \frac{k}{j} F_y(j, k)}{\sum_{j,k} F_y(j, k)}$$

where $F_x(j,k)$ and $F_y(j,k)$ are the magnitude squared of the two-dimensional Fourier transforms of the x and y functions, respectively.

In one implementation of this step, the two functions F(j,k) are passed through a thresholding warping table to remove the effects of noise. In another possible implementation, the summation is only over those pixels in the two-dimensional Fourier domain which correspond to non-zero velocities. This is equivalent to the high pass "wall filter" installed in conventional Doppler echoscopes which removes the effect of stationary and slow-moving reflectors such as vessel walls.

Figure 3:
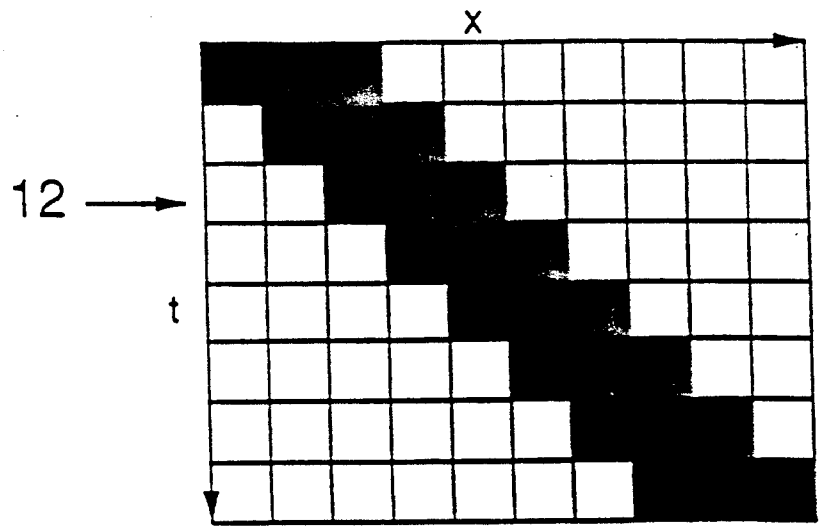
FIGS 3 and 4 are a pair of drawings, used to demonstrate one way of calculating velocity for a given projection function.
Figure 4:
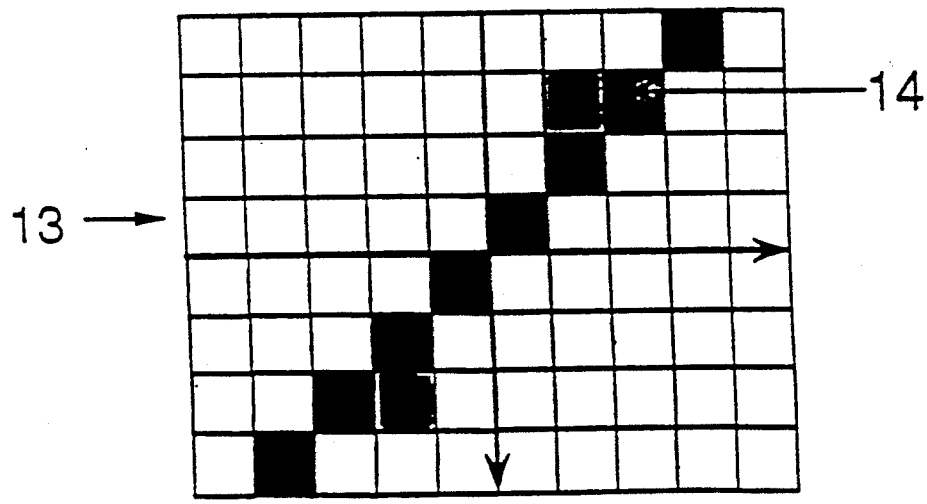

A graphical illustration of the computation technique is shown in FIGS. 3 and 4. The plot of FIG. 3 represents the x projection of a single scatterer moving across a cell. The horizontal axis is x (the line of sight number in the scans) and the vertical axis is t, the scan (or frame) number. The y projection would have a similar appearance. The plot of FIG. 4 is the two-dimensional Fourier transform of the upper plot. The non-zero pixels (for example, pixels 14) are arranged along a line having a slope which depends on the velocity of the scatterer. The actual mean velocity components are calculated using an algorithm such as that described above.

Having obtained values of the two components of velocity $v_x$ and $v_y$, the absolute magnitude of the velocity in the x,y plane may be calculated from the relationship $$|v| = \sqrt{(<v_x>^2 + <v_y>^2)}$$

This quantity ($|v|$) may be displayed as a color modulation of the display. Alternatively, the display may feature depictions of arrows or similar objects whose magnitude and direction correspond to the magnitude and direction of the two dimensional velocity in the cell. The scanning, image observation, data processing and display of velocity are then carried out for another of the sub-images or cells 4.

FIG. 5 shows a display which has been produced following the application of the invention to a blood vessel 15, with the region of interest 16 consisting of a line crossing the vessel (which was drawn by the operator). A group of cells has been generated at the region of interest and, for each cell, an arrow 17 is drawn and updated frequently. The magnitude and direction of each arrow 17 corresponds to the magnitude and direction of the blood flow through its associated cell.

By way of summary, in a normal implementation of the present invention, the sequence of operations will be as follows:

1. The operator selects a region of interest from a B-mode scan. This may be a two-dimensional area of the scan, or a short line segment along which the vector flow characteristics are required.

2. (Optional) In a linear array implementation, the echoscope selects a direction for the lines of sight which minimises the number of adjacent lines of sight intersecting the region of interest.

3. The boundaries of a number of sub-images or "cells", each containing several lines of sight, and each approximately square, are determined. The cells cover the region of interest. The boundaries are chosen so that if a given line of sight passes through a group of several cells, then all lines of sight passing through one of the group pass through all the group.

4. Each cell is scanned a number of times (preferably at least four times). The scans are repeated at the maximum possible frame rate. Additional cells lying along the same group of lines of sight are scanned simultaneously.

5. The reflected signals from each cell are envelope detected and for each scan of a cell, the sum of all lines is calculated and written to one buffer (the y buffer) and the sum of all elements in each line of sight is calculated and written to a second buffer (the x buffer). After several scans of the cell, each of the x and y buffers contains a two-dimensional array of numbers (that is, one one-dimensional array of numbers for each scan of the cell).

6. In the preferred mode of operation, a two-dimensional Fourier transform of each of the x and y buffers is calculated, and its magnitude squared is computed. The two velocity components are calculated and an appropriate indicator of the two-dimensional velocity vector is displayed on the part of the image corresponding to the cell.

7. The calculation in steps 5 and 6 is repeated on all cells intersected by the same lines of sight, which were therefore scanned simultaneously.

8. Steps 4, 5, 6 and 7 are then repeated for other cells not lying along the same group of lines of sight.

9. After producing or updating the flow vector for all of the cells, the conventional ultrasound image may be updated (although this step may be carried out less frequently, if desired).

10. Steps 4 to 9 are then repeated continually, providing a real time display of the liquid flow vector at several points in the image.

If the velocity component in the z-direction of the liquid flowing through the cells is zero, it is possible to obtain the absolute velocity vector of the liquid flowing through the region of interest by summing the two-dimensional (x,y) velocity vectors for each cell of the selected region, provided the chosen cells have common boundaries and do not overlap.

It should be appreciated that although a specific implementation of the present invention has been described above with reference to the accompanying drawings, variations to and modifications of that implementation may be made without departing from the present inventive concept.

I claim:

1. A method of determining the two-dimensional velocity vector of liquid flowing through a region which is included in a B-mode ultrasonic echoscopy display of at least a part of an object, said B-mode display being created from an analysis of the ultrasonic echoes received from a beam of ultrasonic energy which is scanned over said at least part of said object, said scanning being effected by the sequential transmission into said object of said beam of ultrasonic energy along a plurality of lines of sight, each line of sight being spatially displaced relative to its preceding, adjacent line of sight, said method comprising the steps of
   (a) selecting, from said B-mode display, a plurality of small cells within said region, each cell being intersected by a plurality of said lines of sight;
   (b) for a selected one of said cells, scanning the ultrasonic beam at least twice in rapid succession over the lines of sight which pass through the cell and, for each scan, subjecting the signals reflected from scatterers within the cell to conventional video processing and producing a two dimensional brightness function S(x,y), and subsequently creating a data set S(x,y,t) of the image of the cell;
   (c) for the selected cell, integrating the data set S(x,y,t) separately with respect to x and y, by projecting S(x,y,t) onto the (x,t) and (y,t) planes to obtain projected functions $S_x(x,t)$ and $S_y(y,t)$, respectively;
   (d) for the selected cell, determining, from said projected functions $S_x(x,t)$ and $S_y(y,t)$, the average velocity of the scatterers within the cell, and hence of the liquid flowing through the cell, (i) in the x-direction ($<v_x>$) and (ii) in the y-direction ($<v_y>$);
   (e) for the selected cell, determining, from the average velocity in the x-direction and the average velocity in the y-direction, the two-dimensional velocity vector of the liquid flowing through the cell; and
   (f) repeating steps (b), (c), (d) and (e) for another one of the cells.

2. A method as defined in claim 1, in which step (d) is effected by computing the two-dimensional Fourier transforms of the functions $S_x(x,t)$ and $S_y(y,t)$, and then the squared magnitudes of the two dimensional Fourier transforms, and performing a summation over the pixels in the two-dimensional Fourier domains, thus determining the average velocities in the x-direction and the y-direction by applying the formulae $$<v_x> = \frac{\sum_{j,k} \frac{\delta x}{\delta t} \frac{k}{j} F_x(j,k)}{\sum_{j,k} F_x(j,k)}$$

and $$<v_y> = \frac{\sum_{j,k} \frac{\delta y}{\delta t} \frac{k}{j} F_y(j,k)}{\sum_{j,k} F_y(j,k)}$$

where (j,k) are the element numbers in the two dimensional Fourier transforms, $\delta x$ is the sampling interval in x, $\delta y$ is the sampling interval in y, $\delta t$ is the time between sequential scans of the ultrasonic beam in step (b), and $F_x(j,k)$ and $F_y(j,k)$ are the magnitude squared of the two-dimensional Fourier transforms in the $S_x$ and $S_y$ functions, respectively.

3. A method as defined in claim 1 including the additional step of displaying the magnitude of the two-dimensional velocity vector determined for each cell on the said B-mode display.

4. A method as defined in claim 1 including the additional step of displaying the magnitude and direction of the two-dimensional velocity vector determined for each cell on said B-mode display.

5. A method as defined in claim 1 including the additional step, when the flow of liquid in the Z-direction (which is orthogonal to both the x-direction and the Y-direction) is zero, of calculating the three-dimensional flow vector of the liquid flowing through said region.

6. A method as defined in claim 1 in which, in step (b) of claim 1, the scanning of the ultrasonic beam is effected at least four times.

7. A method as defined in claim 1 in which the boundaries of each of said cells are substantially rectangular or trapezoidal.

8. A method as defined in claim 1 in which said region is a line in a vessel through which the liquid is flowing.

9. Apparatus for obtaining values of the two-dimensional velocity vector of liquid flowing through a region of a vessel, the apparatus comprising
   (a) an echoscope adapted to produce a B-mode echogram of at least part of the vessel which includes said region;
   (b) means for defining a plurality of small cells within the image of the region in the B-mode echogram;
   (c) means associated with the echoscope for scanning a selected one of said cells with a beam of ultrasonic energy by transmitting said beam of ultrasonic energy into said selected cell sequentially along a plurality of lines of sight which intersect said cell, for monitoring signals reflected from ultrasonic scatterers within said selected cell, and for forming a two-dimensional image from the reflected signals, defined by a brightness function $S(x,y)$;

(d) programmed computation means adapted
  (i) to receive a plurality of said brightness functions $S(x,y)$ obtained from sequential scanning of the selected cell with said beam of ultrasonic energy, and to store the resultant data set $S(x,y,t)$;
  (ii) to integrate the data set $S(x,y,t)$ separately with respect to x and y by projecting $S(x,y,t)$ onto the (x,t) and (y,t) planes, and thereby obtain projected functions $S_x(x,t)$ and $S_y(y,t)$, respectively;
  (iii) to determine, from said projected functions $S_x(x, t)$ and $S_y(y,t)$, the average velocity of the scatterers within the cell, and hence of the liquid flowing through the cell, in the x-direction ($<v_x>$) and in the y-direction ($<v_y>$); and
  (iv) to obtain, from the average velocity in the x-direction and the average velocity in the y-direction, the two-dimensional velocity vector of the liquid flowing through the cell; and (e) velocity display means associated with the echoscope to incorporate into said B-mode image a display of the magnitude, or the magnitude and direction, of the two-dimensional velocity vector of liquid flowing through the cell.

10. Apparatus as defined in claim 9, in which said computational means is programmed to integrate the data set $S(x,y,t)$ and determine the average velocity of liquid flowing through a cell in the x-direction and in the y-direction by computing the two-dimensional Fourier transforms of the functions $S_x(x,t)$ and $S_y(y,t)$, and then the squared magnitudes of the two dimensional Fourier transforms, and performing a summation over the pixels in the two-dimensional Fourier domains, thus determining the average velocities in the x-direction and the y-direction by the formulae $$<v_x> = \frac{\sum_{j,k} \frac{\delta x}{\delta t} \frac{k}{j} F_x(j, k)}{\sum_{j,k} F_x(j, k)}$$

and $$<v_y> = \frac{\sum_{j,k} \frac{\delta y}{\delta t} \frac{k}{j} F_y(j, k)}{\sum_{j,k} F_y(j, k)}$$

where (j,k) are the element numbers in the two dimensional Fourier transforms, $\delta x$ is the sampling interval in x, $\delta y$ is the sampling interval in y, $\delta t$ is the time between sequential scans of the ultrasonic beam in step (b), and $F_x(j,k)$ and $F_y(j,k)$ are the magnitude squared of the two-dimensional Fourier transforms in the $S_x$ and $S_y$ functions, respectively.

* * * * *